(12) United States Patent
DeRosa et al.

(10) Patent No.: US 6,372,000 B1
(45) Date of Patent: Apr. 16, 2002

(54) HYDROCARBYL POLYOXYALKYLENE AMINOALCOHOL AND FUEL COMPOSITION CONTAINING SAME

(75) Inventors: Thomas F. DeRosa, Wallingford, CT (US); Joseph M. Russo, Katy, TX (US); Benjamin J. Kaufman, Hopewell Junction, NY (US); James R. Ketcham, Salt Point, NY (US); Richard V. Kessler, Wappingers Falls, NY (US); Frank J. DeBlase, Hopewell Junction, NY (US)

(73) Assignee: Texaco Inc., White Plains, NY (US)

( * ) Notice: Subject to any disclaimer, the term of this patent is extended or adjusted under 35 U.S.C. 154(b) by 0 days.

(21) Appl. No.: 09/450,952

(22) Filed: Nov. 30, 1999

Related U.S. Application Data

(63) Continuation-in-part of application No. 09/090,279, filed on Jun. 4, 1998, now abandoned.

(51) Int. Cl.⁷ ................................................. C10L 1/22
(52) U.S. Cl. ........................... 44/424; 44/434; 564/443; 564/505
(58) Field of Search .................... 44/434, 424; 564/443, 564/505

(56) References Cited

U.S. PATENT DOCUMENTS

| | | |
|---|---|---|
| 3,440,029 A | 4/1969 | Little et al. |
| 4,261,704 A | 4/1981 | Langdon |
| 4,460,379 A | 7/1984 | Sweeney et al. |
| 4,526,587 A | 7/1985 | Campbell |
| 4,568,358 A | 2/1986 | Courtney |
| 4,604,103 A | 8/1986 | Campbell |
| 4,747,851 A | 5/1988 | Sung et al. |
| 5,112,364 A | 5/1992 | Rath et al. |
| 5,213,585 A | 5/1993 | Oppenlaender et al. |
| 5,234,478 A | 8/1993 | Su et al. |
| 5,383,942 A | 1/1995 | Su et al. |
| 5,527,364 A | 6/1996 | Russo et al. |
| 5,616,811 A | 4/1997 | Vipond et al. |
| 5,789,490 A | * 8/1998 | Chang .................... 525/403 |
| 6,063,145 A | 5/2000 | Larkin et al. ............... 44/434 |
| 6,060,625 A | * 9/2000 | Su et al. |

FOREIGN PATENT DOCUMENTS

| | | |
|---|---|---|
| EP | 0 356 725 | 3/1990 |
| EP | 0 887 401 | 12/1998 |
| EP | 0 962 479 | 12/1999 |
| FR | 2 402 473 | 4/1979 |
| WO | WO 97/12928 | 4/1997 |
| WO | WO 97/30103 | 8/1997 |

\* cited by examiner

*Primary Examiner*—Margaret Medley
(74) *Attorney, Agent, or Firm*—Morris N. Reinisch; Dilworth & Barrese

(57) ABSTRACT

A hydrocarbyl polyoxyalkylene aminoalcohol of the general formula

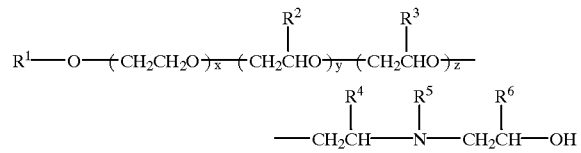

wherein $R^1$ is an alkyl, an alicyclic or an alkylalicyclic radical having from about 4 to about 30 carbon atoms or an alkylaryl where the alkyl group is from about 4 to about 30 carbon atoms; x is an integer from 0 to about 5, y is an integer from 1 to about 49, z is an integer from 1 to about 49 and the sum of x+y+z is equal to 3 to about 50; $R^2$ and $R^3$ each is different and is an alkyl group of from 1 to 4 carbon atoms and each oxyalkylene radical can be any combination of repeating oxyalkylene units to form random or block copolymers; $R^4$ is the same as $R^2$ or $R^3$; $R^5$ is hydrogen or

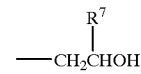

where $R^7$ is hydrogen or an alkyl group of from 1 to 5 carbon atoms and $R^6$ is hydrogen or an alkyl group of from 1 to 5 carbon atoms and an internal combustion engine fuel composition containing same are provided.

41 Claims, No Drawings

HYDROCARBYL POLYOXYALKYLENE AMINOALCOHOL AND FUEL COMPOSITION CONTAINING SAME

IN THE CROSS-REFERENCE TO RELATED APPLICATIONS

This application is continuation-in-part application of U.S. application Ser. No. 09/090,279 filed Jun. 4, 1998, now abandoned.

BACKGROUND OF THE INVENTION

This invention relates to a hydrocarbyl polyoxyalkylene aminoalcohol and to an internal combustion engine fuel composition containing same.

The combustion of fuel in an internal combustion engine typically results in the formation and accumulation of deposits on various parts of the combustion chamber and on the fuel intake and exhaust systems of the engine. The presence of these deposits in the combustion chamber often result in the following problems: (1) reduction in the operating efficiency of the engine; (2) inhibition in the heat transfer between the combustion chamber and the engine cooling system; and (3) reduction in the volume of the combustion zone which can cause a higher than design compression ratio in the engine. A knocking engine can also result from deposits forming and accumulating in the combustion chamber. A prolonged period of a knocking engine can result in stress fatigue and wear in engine components such as, for example, pistons, connecting rods bearings and cam rods.

The formation and accumulation of intake valve deposits can interfere with valve closing which eventually can result in valve burning. Such deposits can also interfere with valve motion and valve seating which tend to reduce the volumetric efficiency of the engine and limit the maximum design power.

Deposits can also collect in the tubes and runners that are part of the exhaust gas recirculation (EGR) flow. The collection of these deposits can reduce the EGR flow. This will result in a knocking engine and an increase in nitric oxide emissions.

In view of the foregoing problems associated with the formation and accumulation of deposits in the combustion chamber and fuel intake and exhaust systems of an internal combustion engine, efforts have been made to develop fuel additives which will inhibit the deposition of deposits in the engine. Illustrative of such fuel additives are the amido alkanolamines of U.S. Pat. Nos. 5,234,478 and 5,383,942 and the alkylphenoxypolyoxyalkylene amine lactones of U.S. Pat. No. 5,527,364.

SUMMARY OF THE INVENTION

In accordance with the present invention, a hydrocarbyl random or block polyoxyalkylene aminoalcohol is provided which possesses the general formula

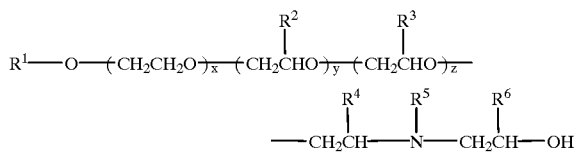

wherein $R^1$ is an alkyl, an alicyclic or an alkylalicyclic radical having from about 4 to about 30 carbon atoms or an alkylaryl where the alkyl group is from about 4 to about 30 carbon atoms; x is an integer from 0 to about 5, y is an integer from 1 to about 49, z is an integer from 1 to about 49 and the sum of x+y+z is equal to 3 to about 50; $R^2$ and $R^3$ each is different and is an alkyl group of from 1 to 4 carbon atoms and each oxyalkylene radical can be any combination of repeating oxyalkylene units to form random or block copolymers; $R^4$ is the same as $R^2$ or $R^3$; $R^5$ is hydrogen or

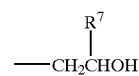

where $R^7$ is hydrogen or an alkyl group of from 1 to 5 carbon atoms; and $R^6$ is hydrogen or an alkyl group of from 1 to 5 carbon atoms.

It shall be understood herein that the oxyalkylene groups constituting the polyoxyalkylene chain in the foregoing general formula may contain random or block sequencing.

Further in accordance with this invention, a method for the preparation of the foregoing hydrocarbyl polyoxyalkylene aminoalcohol is provided which comprises reacting a hydrocarbyl random or block polyoxyalkylene amine of the general formula

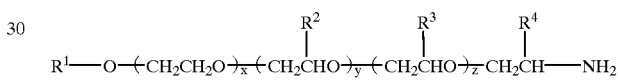

wherein $R^1$ is an alkyl, an alicyclic or an alkylalicyclic radical having from about 4 to about 30 carbon atoms or an alkylaryl where the alkyl group is from about 4 to about 30 carbon atoms; x is an integer from 0 to about 5, y is an integer from 1 to about 49, z is an integer from 1 to about 49 and the sum of x+y+z is equal to 3 to about 50; $R^2$ and $R^3$ each is different and is an alkyl group of from 1 to 4 carbon atoms and each oxyalkylene radical can be any combination of repeating oxyalkylene units to form random or block copolymers; and $R^4$ is the same as $R^2$ or $R^3$ with a 1,2-epoxide of the general formula

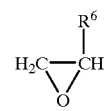

wherein $R^6$ is hydrogen or an alkyl group of from 1 to 5 carbon atoms to provide the product hydrocarbyl random or block polyoxyalkylene aminoalcohol of the general formula

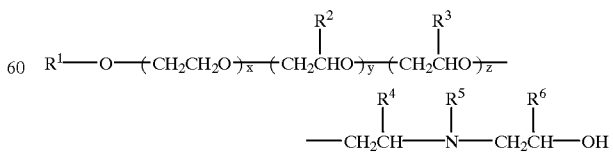

wherein $R^1$, $R^2$, $R^3$, $R^4$, $R^6$, x, y and z have the aforestated meanings and $R^5$ is hydrogen or

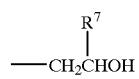

wherein $R^7$ is hydrogen or an alkyl group of from 1 to 5 carbon atoms.

Still further in accordance with the present invention, a fuel composition is provided which comprises a major amount of an internal combustion engine fuel and a fuel combustion deposit-inhibiting amount of at least one hydrocarbyl random or block polyoxyalkylene aminoalcohol of the general formula

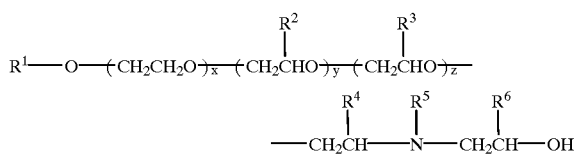

wherein $R^1$, $R^2$, $R^3$, $R^4$, $R^5$, $R^6$, x, y and z have the aforestated meanings.

Yet further in accordance with the present invention, a method for inhibiting the deposition of fuel combustion deposits in an internal combustion engine is provided which comprises operating the engine employing as the fuel therefor a fuel composition which comprises a major amount of an internal combustion engine fuel and a fuel combustion deposit-inhibiting amount of at least one hydrocarbyl random or block polyoxyalkylene aminoalcohol of the general formula

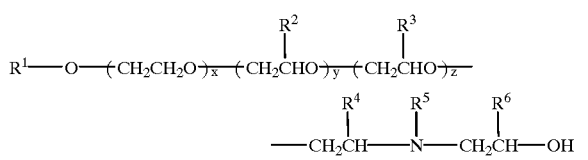

wherein $R^1$, $R^2$, $R^3$, $R^4$, $R^5$, $R^6$, x, y and z have the aforestated meanings.

DESCRIPTION OF THE PREFERRED EMBODIMENTS

The hydrocarbyl random or block polyoxyalkylene aminoalcohol of this invention possesses the general formula

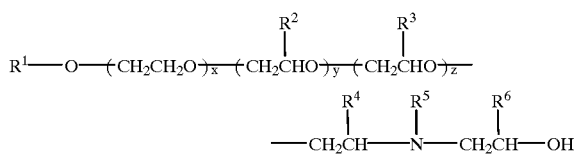

wherein x is an integer from 0 to about 5, y is an integer from 1 to about 49 preferably from about 5 to about 40 and more preferably from about 5 to about 10, z is an integer from 1 to about 49, preferably from about 5 to about 40 and more preferably from about 5 to about 10 and the sum of x+y+z is equal to 3 to about 50; $R^1$ is an alkyl, an alicyclic or an alkylalicyclic radical having from about 4 to about 30 carbon atoms or an alkylaryl where the alkyl group is from about 4 to about 30 carbon atoms, including, by way of illustration, unsubstituted straight or branched aliphatic, cycloaliphatic and aromatic groups and cycloaliphatic and aromatic groups substituted with one or more straight or branched aliphatic, cycloaliphatic and/or aromatic groups. Thus, for example, $R^1$ can be represented by-the general formula

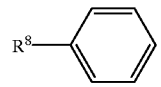

wherein $R^8$ is a hydrocarbyl group of from about 4 to about 30 carbon atoms including, by way of example, a monovalent aliphatic radical having from about 6 to about 24 carbon atoms, preferably from about 8 to about 20 carbon atoms and more preferably from about 9 to about 18 carbon atoms. $R^2$ and $R^3$ each is different and is an alkyl group of from 1 to 4 carbon atoms and each oxyalkylene radical can be any combination of repeating oxyalkylene units to form random or block copolymers with the random copolymers being preferred for use herein; $R^4$ is the same as $R^2$ or $R^3$; $R^5$ is hydrogen or

wherein $R^7$ is hydrogen or an alkyl group of from 1 to 5 carbon atoms; and $R^6$ is hydrogen or an alkyl group of from 1 to 5 carbon atoms. The preferred hydrocarbyl polyoxyalkylene aminoalcohol for use herein as a fuel additive is the random co-polymer 4-n-nonylphenoxypoly-(propylene oxide-co-butylene oxide)-(2-(N-butylalcohol)-amine-1-butyl ether, i.e., a monoalkoxylated product, represented by the formula

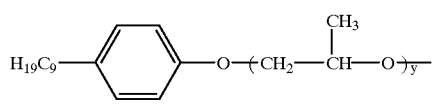

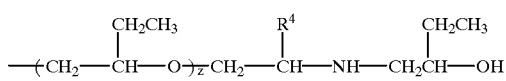

wherein the average value of y is from about 7 to about 8, the average value of z is about half that of y, i.e., from about 3.5 to about 4, with the ratio of y to z being from about 1 to about 3 and preferably from about 1.5 to about 2, $R^4$ is —$CH_3$ or —$CH_2CH_3$ and the propylene/butylene oxides are incorporated as random copolymers.

The foregoing hydrocarbyl polyoxyalkylene aminoalcohol of this invention can be obtained by reacting a hydrocarbyl polyoxyalkylene amine of the general formula

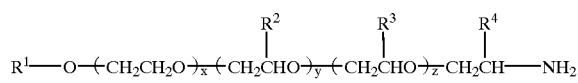

wherein $R^1$, $R^2$, $R^3$, $R^4$, x, y and z have the aforestated meanings with a 1,2-epoxide of the general formula

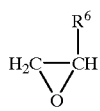

wherein $R^6$ has the aforestated meaning.

Representatives of the hydrocarbyl polyoxyalkylene amine are known in the art, e.g., in U.S. Pat. No. 5,383,942, the contents of which are incorporated by reference herein. In general, the hydrocarbyl polyoxyalkylene amine can be prepared by first reacting an alkylaryl or a hydrocarbyl alcohol represented by the general formula

wherein $R^1$ has the aforestated meaning with at least two 1,2-epoxides represented by the general formulae

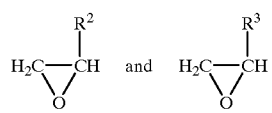

wherein $R^2$ and $R^3$ have the aforestated meanings. Optionally, a small amount of ethylene oxide, e.g., up to about 35 percent, can be added to the foregoing reaction to provide a hydrocarbyl polyoxyalkylene hydroxide represented by the general formula

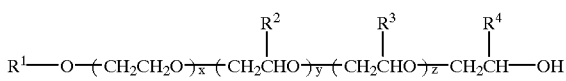

wherein $R^1$, $R^2$, $R^3$, $R^4$, x, y and z have the aforestated meanings. Preferred 1,2-epoxides for use herein include, but are not limited to, ethylene oxide, propylene oxide, butylene oxide and the like.

The hydrocarbyl alcohol and at least two 1,2-epoxides are advantageously reacted to form the hydrocarbyl polyoxyalkylene hydroxide in a mole ratio ordinarily ranging from about 5 to about 30 and preferably from about 10 to about 20. The reaction is ordinarily conducted at a temperature ranging from about 90° C. to about 120° C. and preferably from about 100° C. to about 115° C. The time for preparing the hydrocarbyl polyoxyalkylene hydroxide, under preferred parameters, will generally not exceed 8 hours.

The hydrocarbyl polyoxyalkylene hydroxide is then reacted with ammonia to provide the hydrocarbyl polyoxyalkylene amine. In general, the amount of ammonia reacted with the hydrocarbyl polyoxyalkylene hydroxide will range from about 1.0 cc/min to about 3.0 cc/min and preferably from about 1.5 cc/min to about 2.5 cc/min. The temperature of this reaction will ordinarily range from about 160° C. to about 209° C. and preferably from about 190° C. to about 208° C.

The hydrocarbyl polyoxyalkylene amine is then reacted with 1,2-epoxide or mixtures thereof to form the desired hydrocarbyl polyoxyalkylene aminoalcohol utilized herein. Suitable 1,2-epoxides to react with the hydrocarbyl polyoxyalkylene amine include, but are not limited to, ethylene oxide, propylene oxide, butylene oxide, pentylene oxide, hexylene oxide and heptylene oxide. A preferred 1,2-epoxide for use herein is butylene oxide. Generally, the hydrocarbyl polyoxyalkylene amine and the 1,2-epoxide are advantageously reacted to provide a product mixture containing the product hydrocarbyl polyoxyalkylene aminoalcohol. During this condensation reaction, the predominant product formed in the product mixture is a monobutoxylated amine. As one skilled in the art will readily appreciate, other products are unavoidably present in the product mixture during this reaction. For example, in addition to providing the predominant mono-butoxylated amine product, the product mixture may contain from about 0.1 weight percent up to about 25 weight percent apiece of (a) unreacted hydrocarbyl polyoxyalkylene amine and/or (b) a di-butoxylated amine.

In general, the 1,2-epoxide is reacted with the hydrocarbyl polyoxyalkylene amine in a mole ratio ranging from about 1:1 to about 50:1 and preferably from about 1:1 to about 7:1. An especially advantageous molar ratio range is from about 2:1 (employed in Example 1, infra) to about 4:1 (employed in Example 2, infra). The temperature for this reaction will ordinarily range from about 140° C. to about 190° C. and preferably from about 150° C. to about 180° C. The time period for this reaction will typically not exceed 8 hours.

The hydrocarbyl polyoxyalkylene aminoalcohol of this invention is particularly useful as an additive in an internal combustion engine fuel composition to inhibit the deposition of fuel combustion deposits in the combustion chamber and intake valves and exhaust system of an internal combustion engine. Generally, the fuel composition will contain a major amount of an internal combustion engine fuel and an effective fuel combustion deposit-inhibiting amount of at least one hydrocarbyl polyoxyalkylene aminoalcohol of this invention.

Preferred fuel compositions are those intended for, but not limited to, use in spark ignition internal combustion engines. Such fuel compositions, i.e., gasoline base stocks, ordinarily contain a mixture of hydrocarbons boiling in the gasoline boiling range of from about 90° F. to about 370° F. This fuel can consist of straight or branched chain paraffins, cycloparaffins, olefins, aromatic hydrocarbons, or mixtures thereof. The fuel can be derived from among others, straight run naphtha, polymer gasoline, natural gasoline, or from catalytically cracked or thermally cracked hydrocarbons and catalytically reformed stock. Generally, the composition and octane level of the fuel are not critical and any conventional fuel can be employed herein.

In general, the amount of the hydrocarbyl polyoxyalkylene aminoalcohol employed in the fuel composition as a fuel additive can range from about 10 to about 2000 pounds per thousand barrels (PTB), preferably from about 20 to about 1000 PTB and more preferably from about 40 PTB to about 300 PTB.

In the fuel composition, other fuel additives can be employed with the additive of this invention, including, for example, antiknock agents such as tetraethyl lead compounds, anti-icing additives, antioxidants, metal deactivators, demulsifiers and the like.

The following Examples 1–4 are illustrative of the preparation of the hydrocarbyl polyoxyalkylene aminoalcohol of this invention and its use as a fuel additive for inhibiting the deposition of fuel combustion deposits in an internal combustion engine. Additionally, Comparative Examples 1–5 (all of which are outside the scope of this invention) are illustrative of the preparation of the compounds obtained from Examples 1 and 2 of U.S. Pat. No. 4,261,704 and Example 1 from each of U.S. Pat. Nos. 4,460,379; 4,526,587 and 4,604,103 and comparing the use of these compounds as a fuel additive for inhibiting the deposition of fuel combustion deposits in an internal combustion engine against the fuel additives of Examples 1 and 2 of this invention.

Part I Summary of Examples 1–4

A. Materials

| Example No. | Product Structure |
|---|---|
| 1A | 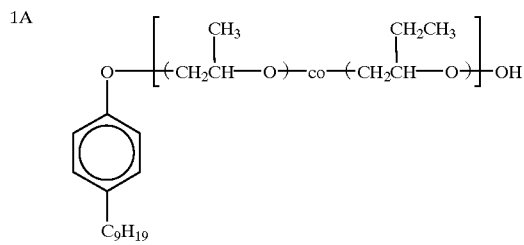 |
| 1B | 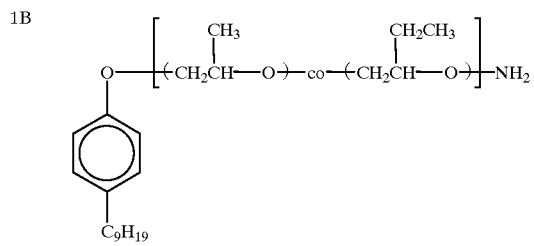 |
| 1C | 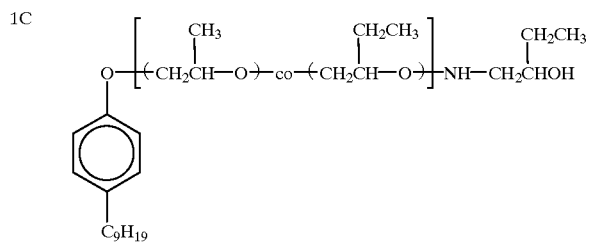 |
| 2 | 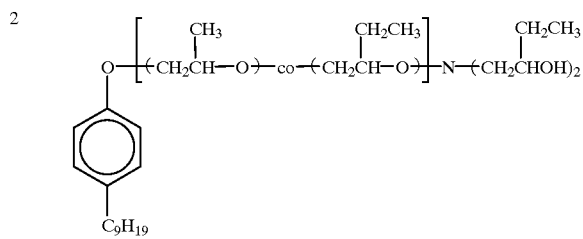 |
| 3A | 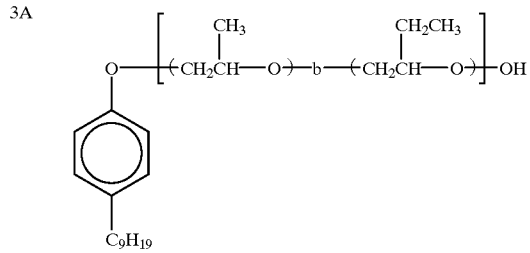 |

| Example No. | Product Structure |
|---|---|
| 3B | (structure with CH$_3$/CH$_2$CH$_3$ block co-polyether terminating in NH$_2$, with C$_9$H$_{19}$-phenyl) |
| 3C | (structure with CH$_3$/CH$_2$CH$_3$ block co-polyether terminating in NH—CH$_2$CHOH—CH$_2$CH$_3$, with C$_9$H$_{19}$-phenyl) |
| 4 | (structure with CH$_3$/CH$_2$CH$_3$ block co-polyether terminating in N(CH$_2$CHOH—CH$_2$CH$_3$)$_2$, with C$_9$H$_{19}$-phenyl) |

As one skilled in the art will readily appreciate, the product structures shown above for Examples 1A–1C, 2, 3A–3C and 4 will also possess either propylene or butylene group which bonds to the last propylene oxide or butylene oxide group formed in the polyoxyalkylene chain. This product structure is shown below in each of Examples 1C, 2, 3C and 4.

| Example No. | Additive Status | Distinguishing Structural Components |
|---|---|---|
| 1A | Intermediate-1 | Random co-polyether alcohol |
| 1B | Intermediate-2 | Random co-polyether amine |
| 1C | Experimental Additive-1 | Random co-polyether aminoalcohol |
| 2 | Experimental Additive-2 | Random co-polyether amine |
| 3A | Intermediate-3 | Block co-polyether alcohol |
| 3B | Intermediate-4 | Block co-polyether amine |
| 3C | Experimental Additive-3 | Block co-polyether aminoalcohol |
| 4 | Experimental Additive-4 | Block co-polyether amine |

B. Preparation of the Random Copolymers of this Invention.

Example 1A

Preparation of 4-n-nonylphenoxypoly (propylene oxide-co-butylene oxide)-(2-hydroxyl)-1-butyl ether.

Into a 10 gallon kettle were charged 4.2 pounds of nonylphenol and 57 grams of 50 percent aqueous potassium hydroxide. The reactor was then purged with prepurified nitrogen. Maintaining a nitrogen purge, the reactor was heated to 100° C. and the nonylphenolate salt dried to a water content of less than 0.1 percent using both vacuum and nitrogen stripping. A mixture of 10.3 lbs. propylene oxide and 6.9 lbs. 1,2-butylene oxide was then reacted at 115° C. at 90 psig over a six hour period. The reaction mixture was then digested at 115–120° C. to an equilibrium pressure and purged with nitrogen for 30 minutes. The alkaline product was then neutralized at 95° C. by stirring for two hours with 173 grams Magnesol 30/40 absorbent which was added in an aqueous slurry. The neutralized product was then vacuum stripped to a minimum pressure at 100–120° C., nitrogen stripped and filtered. Properties of the finished product are given in Table I below.

TABLE I

|  | Properties |
| --- | --- |
| Acid no. mg KOH/g | <0.01 |
| Hydroxyl no. mg KOH/g | 56 |
| Water, wt. % | 0.1 max |
| Color, Pt—Co | 150 max |
| Viscosity, 40° C., eST. | 132 |

Example 1B

Preparation of 4-n-nonylphenoxypoly (propylene oxide-co-butylene oxide)-(2 amine)-1-butyl ether.

0.127 lb/hr of the product of Example 1A, 0.169 lb/hr of ammonia and 6 L/hr of hydrogen were added to the reactor filled with 455 grams of a Raney nickel catalyst. The reactor was at a pressure of 2750 psig and a temperature of 205° C. The crude reactor effluent was charged to a clean dry kettle. It was then nitrogen stripped to 75° C., placed under vacuum and heated to 100° C. Analysis of the product is given in Table II.

TABLE II

|  | meq/gram |
| --- | --- |
| Total acetylatables | 1.0 |
| Total amine | 0.96 |
| Primary amine | 0.96 |

Example 1C

Preparation of 4-n-nonylphenoxypoly (propylene oxide-co-butylene oxide)-(2-(N-butylalcohol) amine)-1-butyl ether.

To a 1 gallon autoclave equipped with a thermometer, stirrer and nitrogen outlet, 2000 grams of the amine product of Example 1B and 274 grams of butylene oxide were charged. The mixture was heated to 160° C. for a period of eight hours. As shown in Table III, the final product had the following analysis.

TABLE III

|  | meq/gram |
| --- | --- |
| Total acetylatables | 1.0 |
| Total amine | 0.9 |

The final product is a mixture of products with the major component being a monoalkoxylated product as represented by the following formula

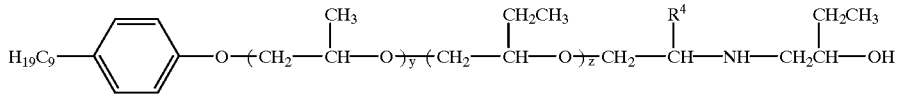
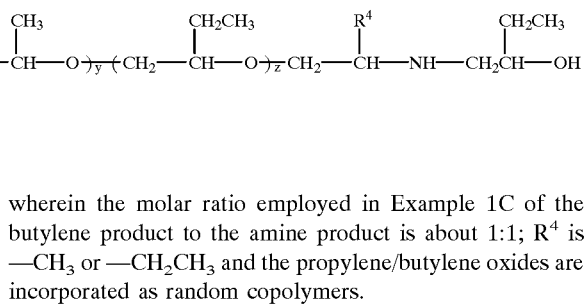

wherein the molar ratio employed in Example 1C of the butylene product to the amine product is about 1:1; $R^4$ is —$CH_3$ or —$CH_2CH_3$ and the propylene/butylene oxides are incorporated as random copolymers.

Example 2

Preparation of 4-n-nonylphenoxypoly (propylene oxide-co-butylene oxide)-(2-(N,N-di-butylalcohol) amine)-1-butyl ether.

To a 2 gallon autoclave with a thermometer, stirrer and nitrogen outlet, 2,000 grams of the amine product of Example 1B and 584 grams of butylene oxide were charged. The mixture was heated to 160° C. for a period of eight hours. As shown in Table IV the final product had the following analysis.

TABLE IV

|  | meq/gram |
| --- | --- |
| Total acetylatables | 1.0 |
| Total amine | 0.9 |

The final product is a mixture of products with the major component being a dialkoxylated product, as represented by the following formula

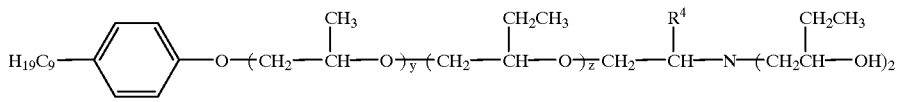

wherein the molar ratio of butylene oxide to the amine product is about 2.4:1; $R^4$ is —$CH_3$ or —$CH_2CH_3$ and the propylene/butylene oxides are incorporated as random copolymers.

C. Preparation of the Block Copolymers of this invention.

Example 3A

Preparation of 4-n-nonylphenoxypoly (propylene oxide-b-butylene oxide)-(2-hydroxyl))-1-butyl ether.

This block copolymer was prepared by sequentially adding and digesting co-reagent epoxides to the reaction chamber using the stoichiometry and work up procedure of Example 1A.

Example 3B

Preparation of 4-n-nonylphenoxypoly (propylene oxide-b-butylene oxide)-(2-amino)-1-butyl ether.

This block copolymer was prepared by amination of the product in Example 3A using the procedure of Example 1B.

Example 3C

Preparation of 4-n-nonylphenoxypoly (propylene oxide-b-butylene oxide) -(2-(N-butylalcohol) amine-1-butyl ether.

This block copolymer was prepared by reacting the product of Example 3B with butylene oxide according to the procedure of Example 1C. The final product is a mixture of products with the major component being a monoalkoxylated product as represented by the following formula

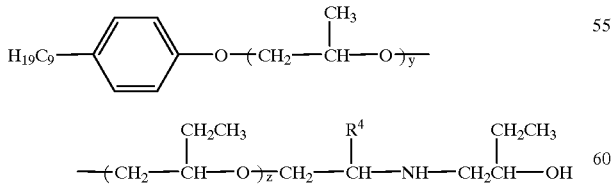

wherein the molar ratio of butylene oxide to the amine product is about 1:1; $R^4$ is —$CH_3$ or —$CH_2CH_3$ and the propylene/butylene oxides are incorporated as block copolymers.

Example 4

Preparation of 4-n-nonylphenoxypoly (propylene oxide-b-butylene oxide)-(2-(N,N-di-butylalcohol) amine-1-butyl ether.

This block copolymer was prepared by reacting the product of Example 3B with butylene oxide according to the procedure of Example 2. The final product is a mixture of products with the major component being a dialkoxylated product as represented by the following formula

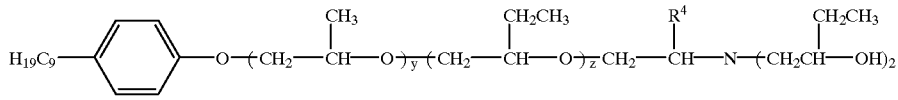

wherein the molar ratio of butylene oxide to the amine product is about 2.4:1; $R^4$ is —$CH_3$ or —$CH_2CH_3$ and the propylene/butylene oxides are incorporated as block copolymers.

Part II Summary of Comparative Examples 1–11

A. Materials

| Comparative Example No. | Product Structure |
|---|---|
| 1 | 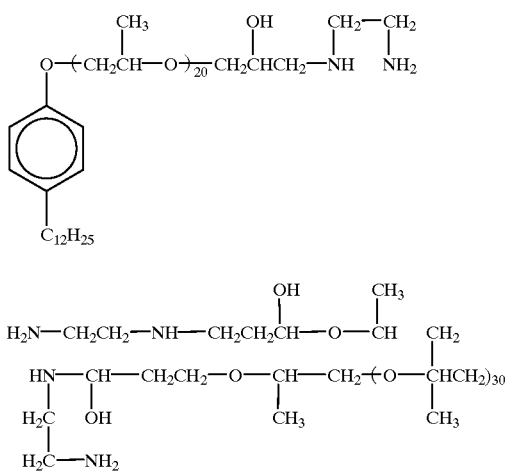 |
| 2 | |

-continued

| Comparative Example No. | Product Structure |
|---|---|
| 3 | $C_{10-12}H_{21-25}OCH_2CH(CH_3)-OCH_2CH-N(CH_2CH_2OH)_2$ |
| 4 | $H_2N-CH_2CH_2-NH-CH_2CH_2-O-(CH_2CH(CH_2CH_3)-O)_{16}-CHCH_2O$; $HO-CH_2CH-C_{14}H_{29}$ (with $CH_2CH_3$ branches) |
| 5 | $H_2N-CHCH_2-NH-CH_2CH_2-O-(CH_2CH(CH_2CH_3)-O)_9-CHCH_2O$; $CH_2$; $(CH_3)_2CHCH_2-C(CH_3)_2$ (with $CH_2CH_3$ branches) |

| Comparative Example No. | Distinguishing Structural Components |
|---|---|
| 1 | Homopolyether diamine |
| 2 | Homopolyether polyamine dialcohol |
| 3 | Aliphatic diether amino dialcohol |
| 4 | Homopolyether amino alcohol |
| 5 | Homopolyether amine |

The product structure formed in Comparative Examples 6–11 is represented by the following formula

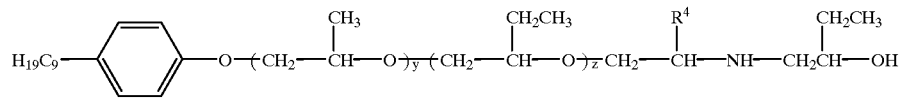

wherein $R^4$ is $-CH_3$ or $-CH_2CH_3$, the oxyalkylene units are incorporated as random copolymers and the molar ratio of y to z for each of Comparative Examples 6–11 are set forth below.

| Comparative Example No. | Moles of Propylene Oxide (y) and Butylene Oxide (z) | | Distinguished Co-polyether |
|---|---|---|---|
| 6 | y = 14.2 | z = 0 | Homopolyether amino alcohol |
| 7 | y = 0 | z = 14.2 | Homopolyether amino alcohol |
| 8 | y = 7.1 | z = 7.1 | Random co-polyether |
| 9 | y = 5.0 | z = 9.2 | Random co-polyether |
| 10 | y = 10.6 | z = 3.3 | Random co-polyether |
| 11 | y = 3.3 | z = 10.6 | Random co-polyether |

B. The following illustrates the preparation of Comparative Examples 1–11.

Comparative Example 1

The component of this Example was prepared according to the method of Example 1 described in Langdon U.S. Pat. No. 4,261,704.

Comparative Example 2

The component of this Example was prepared according to the method of Example 2 described in Langdon U.S. Pat. No. 4,261,704.

Comparative Example 3

The component of this Example was prepared according to the method of Example 1 described in Sweeney et al. U.S. Pat. No. 4,460,379.

Comparative Example 4

The component of this Example was prepared according to the method of Example 1 described in Campbell of U.S. Pat. No. 4,526,587.

Comparative Example 5

The component of this Example was prepared according to the method of Example 1 described in Campbell U.S. Pat. No. 4,604,5103.

Comparative Examples 6–11

Each of Comparative Examples 6–11 were prepared similarly to the compound of Example 1A–1C except the molar ratios of the propylene oxide and butylene oxide (y and z) employed were varied as shown above in Section A of Part II.

Part III Fuel Additive Evaluation

A. Fuel

The fuel additives of Examples 1 and 2 were then compared to the fuel additives of Comparative Examples 1–5 and to a commercial detergent package by testing these fuel additives as a combustion chamber and intake valve detergent in a fuel composition using a Honda Generator Test to demonstrate each of the fuel additives effectiveness for inhibiting combustion chamber and intake valve deposits. The additized fuel compositions and unadditized fuel composition, i.e, the fuel composition containing the commercial detergent package, are described in Fuel 1 and Fuel 2, respectively.

| FUEL 1 | |
|---|---|
| Test | Characteristics |
| API Gravity 60° F. | 55.5 |
| RVP (psi) | 7.7 |
| Sulfur (PPM) | 304.0 |
| Existent Gum, mg (mg/100 ml) Washed | 2.0 |
| Oxidation Stability Minute | 1440.0 |

-continued

FUEL 1

| Test | Characteristics |
|---|---|
| FIA | |
| Aromatic (vol %) | 33.6 |
| Olefin (vol %) | 12.7 |
| Saturates | 53.7 |
| ASTM Distillation ° F. | |
| IBP | 91.4 |
| 5% | 126.8 |
| 10% | 144.4 |
| 20% | 170.6 |
| 30% | 192.3 |
| 40% | 210.5 |
| 50% | 227.3 |
| 60% | 243.8 |
| 70% | 262.9 |
| 80% | 294.0 |
| 90% | 341.0 |
| 95% | 371.3 |
| FBP | 418.4 |
| Loss % | 1.0 |
| Res % | 1.3 |
| Oxygenates | None |

FUEL 2

| Test | Characteristics |
|---|---|
| API Gravity 60° F. | 55.2 |
| RVP (psi) | 7.6 |
| Sulfur (PPM) | 310.0 |
| Existent Gum, mg (mg/100 ml) Washed | 2.0 |
| Oxidation Stability Minute | 1418.0 |
| FIA | |
| Aromatic (vol %) | 32.9 |
| Olefin (vol %) | 12.5 |
| Saturates | 54.6 |
| ASTM Distillation ° F. | |
| IBP | 87.0 |
| 5% | 123.0 |
| 10% | 144.0 |
| 20% | 177.0 |
| 30% | 199.0 |
| 40% | 215.0 |
| 50% | 228.0 |
| 60% | 240.0 |
| 70% | 256.0 |
| 80% | 287.0 |
| 90% | 344.0 |
| 95% | 375.0 |
| FBP | 423.0 |
| Loss % | 1.4 |
| Res % | 1.1 |
| Oxygenates | None |

B. Honda Generator Test

This test was developed to determine (1) the intake valve detergency of an additive and (2) whether the additive will cause the intake valves to stick.

In small two-cylinder gasoline powered engines, the intake valves accumulate large amounts of fuel combustion deposits which interfere with the operation of the engine. A detergent/dispersant is required to prevent the buildup of these deposits. The Honda Generator Test was developed to measure the activity of a fuel additive in preventing the buildup of intake valve deposits (IVD), i.e., keep clean. The measurements were done in the following two ways: (1) the intake valves at the end of the test were rated using the CRC rating, i.e., a valve with a rating of 10 is perfectly clean and a valve with a rating of 6 or less contains heavy deposit levels, and (2) intake valve deposit weights were obtained. In addition, the Intake System Deposit/Intake Valve Stickiness Test consisted of an electrical generator driven by a current technology gasoline engine which is similar in many characteristics to modern vehicle engines. The generator set design allowed the engine to be easily loaded by using the electrical generator as a dynamometer for the engine. The set operated at a governed speed of 3600 rpm and incorporated a twin cylinder, overhead camshaft and watercooled engine as described below in Table V.

TABLE V

Engine Data for ES6500 Honda Generator

| | |
|---|---|
| Type: 4-stroke | Overhead cam, 2 cylinder |
| Cooling System: | Liquid cooled |
| Displacement: | 359 cc |
| Bore × stroke: | 58 × 68 mm |
| Construction: | Aluminum head and block, fixed cast iron cylinder liners |
| Compression: | 8.5:1 |
| Maximum Power: | 9.1 Kw/3600 rpm |
| Maximum Torque: | 240 kg-cm |
| Fuel System: | Carburetor |

Part IV Test Results

| | | |
|---|---|---|
| A. | Category 1 | Random copolymer |
| | Type-1 | Random copolyether containing 14.2 mole ether having a 1.84 co-monomer ratio |

The test results from Examples 1A–1C and Example 2, Comparative Examples 1–5, and a commercial additive are summarized in Table VI.

TABLE VI

Honda Generator Intake Tests Results

| | Dosage PTB | CRC Valve Rating | IVD Weight (grams) | Stickiness (lbs. of push) |
|---|---|---|---|---|
| Example 1C | 236 | 9.73 | 0.0062 | 0.00 |
| Example 1C | 188 | 9.23 | 0.0072 | 0.20 |
| Example 2 | 236 | 5.00> | 0.1500> | 1.00> |
| Example 1A | 236 | 5.00> | 0.1500> | 1.00> |
| Example 1B | 236 | 7.61 | 0.0090 | 0.60 |
| Comp. Example 1 | 236 | 7.35 | 0.0893 | 0.80 |
| Comp. Example 2 | 236 | 5.00> | 0.1500> | 1.00> |
| Comp. Example 3 | 236 | 7.02 | 0.0910 | 0.90 |
| Comp. Example 4 | 236 | 6.93 | 0.1044 | 1.00 |
| Comp. Example 5 | 236 | 6.42 | 0.1111 | 1.00 |
| Commercial Additive | 236 | 9.43 | 0.0232 | 0.00 |
| Unadditized | 236 | 5.00> | 0.1500> | 1.00> |

It is readily apparent that the fuel composition containing the fuel additive of Example 1C, i.e., the monoalkoxylated product of this invention, at 236 PTB provided excellent CRC ratings with virtually no deposits on the intake valves, i.e., 6.2 mg or less.

Although only marginal detergency was observed for the nonalkoxylated amine, Example 1B, detergency was unobserved for its di-alkoxylated analogue of Example 2. Detergency for Example 1A was not surprisingly absent, since it is expected to behave as a surfactant.

Fuel compositions containing the fuel additives of Comparative Examples 1–5, i.e., the fuel additives of Examples 1 and 2 of U.S. Pat. No. 4,261,704 and Example 1 from each of U.S. Pat. Nos. 4,460,379; 4,526,587; and 4,604,103 (the fuel composition containing the fuel additives outside the scope of this invention), at 236 PTB consistently provided CRC ratings significantly lower than those of Example 1 (fuel compositions containing the fuel additive of this invention) with a substantially greater amount of deposits on the intake valves. Additionally, the commercial additive package at 236 PTB provided CRC ratings below that of the fuel containing the fuel additive of Example 1C with a substantially greater amount of deposits on the intake valves, i.e., 23.2 mg. Thus, the fuel additive of Example 1C, i.e., the monoalkoxylated product of this invention, significantly inhibits the formation of fuel combustion deposits in an internal combustion engine as compared to the above-described fuel additives of U.S. Pat. Nos. 4,261,704; 4,460,379; 4,526,587; and 4,604,103, i.e., Comparative Examples 1–5 which are outside the scope of this invention, with the monoalkoxylated product of Example 1C providing the best results.

Type-2 Random Copolymers Containing 14.2 Mole ether in Various Co-monomer Ratios.

Table VII summarizes monoalkoxylated analogues of Example 1C containing varying ratios of propylene oxide to butylene oxide evaluated for detergency using the Honda Generator Test described above.

TABLE VII

Gasoline Additives

| Sample | Moles Propylene Oxide (y) | Moles Butylene Oxide (z) | Molar Ratio (y:z) | Total Polyether Content (Moles) |
|---|---|---|---|---|
| Example 1C | 9.2 | 5.0 | 1.84:1 | 14.2 |
| Comp. Example 6 | 14.2 | — | N/A | 14.2 |
| Comp. Example 7 | — | 14.2 | N/A | 14.2 |
| Comp. Example 8 | 7.1 | 7.1 | 1:1 | 14.2 |
| Comp. Example 9 | 5.0 | 9.2 | 0.54:1 | 14.2 |
| Comp. Example 10 | 10.6 | 3.3 | 3.21:1 | 14.2 |
| Comp. Example 11 | 3.3 | 10.6 | 0.31:1 | 14.2 |

The test results of additives appearing in Table VII are summarized below in Table VIII.

TABLE VIII

| Sample | Dosage (PTB) | CRC Valve Rating | IVD Weight (g) | Stickiness (lbs of Push) |
|---|---|---|---|---|
| Example 1C | 236 | 9.73 | 0.0062 | 0.0 |
| Example 1C | 188 | 9.29 | 0.0072 | 0.6 |
| Comp. Example 6 | 236 | 8.12 | 0.0844 | 0.6 |
| Comp. Example 7 | 236 | 8.71 | 0.0706 | 0.6 |
| Comp. Example 8 | 236 | 7.68 | 0.0892 | 0.8 |
| Comp. Example 9 | 236 | 7.90 | 0.0853 | 0.7 |
| Comp. Example 10 | 236 | 8.63 | 0.0796 | 0.6 |
| Comp. Example 11 | 236 | 8.21 | 0.0851 | 0.6 |

These data show that the hydrocarbyl polyoxyalkylene aminoalcohol of Example 1C, which possesses a propylene oxide to butylene oxide molar ratio within the scope of this invention, employed as a fuel additive in a fuel composition at 236 PTB and 188 PTB, respectively, provided excellent CRC ratings, i.e, 9.73 and 9.29 respectively, with virtually no deposits on the intake valves, i.e., 6.2 mg and 7.2 mg respectively. Additionally, there was virtually no stickiness for the fuel additive employed at 188 PTB while the fuel additive employed at 236 PTB achieved a stickiness of 0.0. However, the hydrocarbyl polyoxyalkylene aminoalcohols of Comparative Examples 6–11, all of which possess propylene oxide to butylene oxide molar ratios outside the scope of this invention, provided CRC ratings significantly below that of the fuel composition containing the fuel additive of Example 1C, i.e., a CRC rating ranging from 7.68 to 8.71. The fuel containing the fuel additive of Comparative Examples 6–11 also provided substantially greater amounts of deposit on the intake valves, i.e., from 70.6 mg to 89.2 mg. with some stickiness present.

B. Category 2 Block Copolymer

Table IX summarizes the Honda Generator Test for the block copolymer prepared in Examples 3A–3C and 4.

TABLE IX

Honda Generator Intake Test Results

| Sample | Dosage (PTB) | CRC Value Rating | IVD wt. (grams) | Stickiness (lbs. of Push) |
|---|---|---|---|---|
| Example 3C | 236 | 8.18 | 0.0082 | 0.60 |
| Example 4 | 236 | 5.00> | 0.1500> | 1.00> |
| Example 3A | 236 | 5.00> | 0.1500> | 1.00> |
| Example 3B | 236 | 7.01 | 0.0087 | 0.70 |
| Unadditized Fuel | 236 | 5.00> | 0.1500> | 1.00> |

These results empiratically underscore the effects that the alkoxylating block copolyether amine has upon detergency. It can be seen that enhancing fuel detergents may be achieved by monoalkoxylating Example 3B, as shown in Example 3, and eliminated through dialkoxylation, as shown in Example 4. It was anticipated that Example 3A would not behave as a detergent since random or block copolyether alcohols behave as surfactants.

The hydrocarbyl random polyoxyalkylene aminoalcohol of this invention, 4-n-nonylphenoxypoly-(propylene oxide-butylene oxide)-(2-(N-butylalcohol)amino)-1-butyl ether, consisting of 14.2 moles epoxide with a 1.84 co-monomer ratio, has been discovered as a fuel detergent when it is dissolved in gasoline fuel. In addition, it has been discovered that hydrocarbyl polyoxyalkylene aminoalcohol compositions consisting of (a) co-monomer ratios outside the scope of this invention, i.e., outside the co-monomer ratio range of about 1 to about 3, or,(b) containing a N,N-(di-butyl alcohol) amino terminus, are ineffective as detergents.

What is claimed is:

1. A hydrocarbyl polyoxyalkylene aminoalcohol compound of the general formula

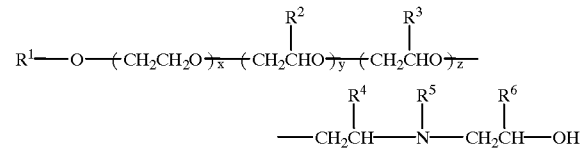

wherein $R^1$ is an alkyl, an alicyclic or an alkylalicyclic radical having from about 4 to about 30 carbon atoms or an alkylaryl where the alkyl group is from about 4 to about 30 carbon atoms; x is an integer from 0 to about 5, y is an integer from 1 to about 49, z is an integer from 1 to about 49 and the sum of x+y+z is equal to 3 to about 50; $R^2$ and $R^3$ each is different and is an alkyl group of from 1 to 4 carbon atoms and each oxyalkylene radical can be any combination of repeating oxyalkylene units to form random or block copolymers; $R^4$ is the same as $R^2$ or $R^3$; $R^5$ is hydrogen or

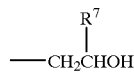

where $R^7$ is hydrogen or an alkyl group of from 1 to 5 carbon atoms and $R^6$ is hydrogen or an alkyl group of from 1 to 5 carbon atoms.

2. The compound of claim 1 wherein $R^1$ is an alkylaryl where the alkyl group is from about 6 to about 30 carbon atoms.

3. The compound of claim 1 wherein $R^2$ is methyl, $R^3$ is ethyl, $R^5$ is hydrogen and $R^6$ is ethyl.

4. The compound of claim 3 wherein x is equal to 0 and the ratio of y to z is from about 1.5 to about 2.

5. The compound of claim 3 wherein x is equal to 0, the oxyalkylene units are incorporated as random copolymers and the ratio of y to z is from about 1.5 to about 2.

6. A random hydrocarbyl polyoxyalkylene aminoalcohol copolymer of the general formula

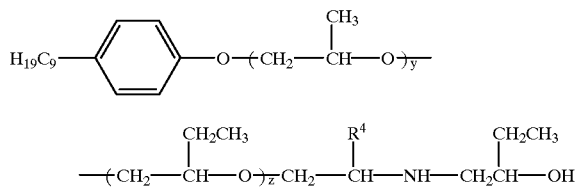

wherein y is an integer from about 5 to about 10, z is an integer from about 5 to about 10 and $R^4$ is —$CH_3$ or —$CH_2CH_3$.

7. The random copolymer of claim 6 wherein the ratio of y to z is from about 1 to about 3.

8. The random copolymer of claim 6 wherein the ratio of y to z is from about 1.5 to about 2.

9. A method for the preparation of a hydrocarbyl polyoxyalkylene aminoalcohol which comprises reacting a hydrocarbyl polyoxyalkylene amine of the general formula

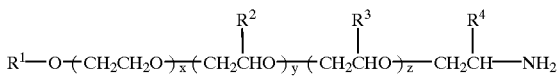

wherein $R^1$ is an alkyl, an alicyclic or an alkylalicyclic radical having from about 4 to about 30 carbon atoms or an alkylaryl where the alkyl group is from about 4 to about 30 carbon atoms; x is an integer from 0 to about 5, y is an integer from 1 to about 49, z is an integer from 1 to about 49 and the sum of x+y+z is equal to 3 to about 50; $R^2$ and $R^3$ each is different and is an alkyl group of from 1 to 4 carbon repeating oxyalkylene units to form random or block copolymers; and $R^4$ is the same as $R^2$ or $R^3$ with a 1,2-epoxide of the general formula

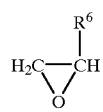

wherein $R^6$ is hydrogen or an alkyl group of from 1 to 5 carbon atoms to provide the product hydrocarbyl polyoxyalkylene aminoalcohol of the general formula

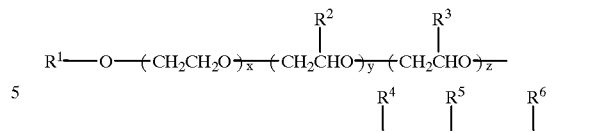

wherein $R^1$, $R^2$, $R^3$, $R^4$, $R^6$, x, y and z have the aforestated meanings and $R^5$ is hydrogen or

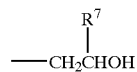

where $R^7$ is hydrogen or an alkyl group of from 1 to 5 carbon atoms.

10. The method of claim 9 wherein $R^1$ is an alkylaryl where the alkyl group is from about 6 to about 24 carbon atoms.

11. The method of claim 9 wherein $R^2$ is methyl, $R^3$ is ethyl, $R^5$ is hydrogen and $R^6$ is ethyl.

12. The method of claim 11 wherein x is equal to 0 and the ratio of y to z is from about 1.5 to about 2.

13. The method of claim 9 wherein the mole ratio of the 1,2-epoxide to the hydrocarbyl polyoxyalkylene amine is from about 2:1 to about 4:1.

14. The method of claim 10 wherein the reaction temperature is from about 140° C. to about 190° C.

15. A fuel composition which comprises a major amount of an internal combustion engine fuel and fuel combustion deposit-inhibiting amount of at least one hydrocarbyl polyoxyalkylene aminoalcohol of the general formula

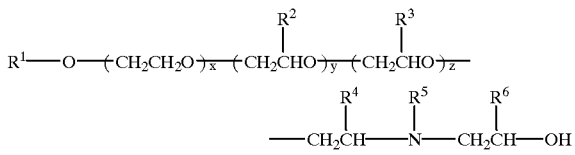

wherein $R^1$ is an alkyl, an alicyclic or an alkylalicyclic radical having from about 4 to about 30 carbon atoms or an alkylaryl where the alkyl group is from about 4 to about 30 carbon atoms; x is an integer from 0 to about 5, y is an integer from 1 to about 49, z is an integer from 1 to about 49 and the sum of x+y+z is equal to 3 to about 50; $R^2$ and $R^3$ each is different and is an alkyl group of from 1 to 4 carbon atoms and each oxyalkylene radical can be any combination of repeating oxyalkylene units to form random or block copolymers; $R^4$ is the same as $R^2$ or $R^3$; $R^5$ is hydrogen or

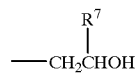

where $R^7$ is hydrogen or an alkyl group of from 1 to 5 carbon atoms and $R^6$ is hydrogen or an alkyl group of from 1 to 5 carbon atoms.

16. The fuel composition of claim 15 wherein $R^1$ is an alkylaryl where the alkyl group is from about 6 to about 30 carbon atoms.

17. The fuel composition of claim 15 wherein $R^2$ is methyl, $R^3$ is ethyl, $R^5$ is hydrogen and $R^6$ is ethyl.

18. The fuel composition of claim 17 wherein x is equal to 0 and the ratio of y to z is from about 1.5 to about 2.

19. The fuel composition of claim 17 wherein x is equal to 0, the oxyalkylene units are formed as random copolymers and the ratio of y to z is from about 1.5 to about 2.

20. The fuel composition of claim 15 wherein the hydrocarbyl polyoxyalkylene aminoalcohol is present in an amount from about 10 PTB to about 2000 PTB.

21. The fuel composition of claim 19 wherein the hydrocarbyl polyoxyalkylene aminoalcohol is present in an amount from about 40 PTB to about 300 PTB.

22. A fuel composition which comprises a major amount of an internal combustion engine fuel and fuel combustion deposit-inhibiting amount of at least one random hydrocarbyl polyoxyalkylene aminoalcohol copolymer of the general formula

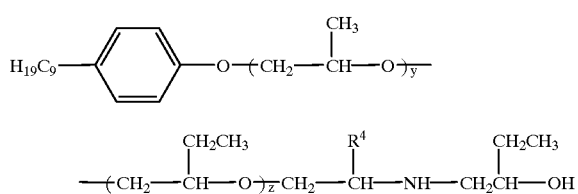

wherein y is an integer from about 5 to about 10, z is an integer from about 5 to about 10 and $R^4$ is $-CH_3$ or $-CH_2CH_3$.

23. The fuel composition of claim 22 wherein the ratio of y to z is from about 1 to about 3.

24. The fuel composition of claim 22 wherein the ratio of y to z is from about 1.5 to about 2.

25. The fuel composition of claim 22 wherein the random copolymer is present in an amount from about 10 PTB to about 2000 PTB.

26. The fuel composition of claim 23 wherein the random copolymer is present in an amount from about 40 PTB to about 300 PTB.

27. A method for inhibiting the deposition of fuel combustion deposits in an internal combustion engine which comprises operating the engine employing as a fuel therefor a fuel composition which comprises a major amount of an internal combustion engine fuel and a fuel combustion deposit-inhibiting amount of at least one hydrocarbyl polyoxyalkylene aminoalcohol of the general formula

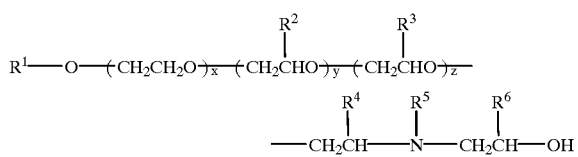

wherein $R^1$ is an alkyl, an alicyclic or an alkylalicyclic radical having from about 4 to about 30 carbon atoms or an alkylaryl where the alkyl group is from about 4 to about 30 carbon atoms; x is an integer from 0 to about 5, y is an integer from 1 to about 49, z is an integer from 1 to about 49 and the sum of x+y+z is equal to 3 to about 50; $R^2$ and $R^3$ each is different and is an alkyl group of from 1 to 4 carbon atoms and each oxyalkylene radical can be any combination of repeating oxyalkylene units to form random or block copolymers; and $R^4$ is the same as $R^2$ or $R^3$; $R^5$ is hydrogen or

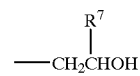

where $R^7$ is hydrogen or an alkyl group of from 1 to 5 carbon atoms and $R^6$ is hydrogen or an alkyl group of from 1 to 5 carbon atoms.

28. The method of claim 27 wherein $R^1$ is a alkylaryl where the alkyl group is from about 6 to about 30 carbon atoms.

29. The method of claim 27 wherein $R^2$ is methyl, $R^3$ is ethyl, $R^5$ is hydrogen and $R^6$ is ethyl.

30. The method of claim 29 wherein x is equal to 0 and the ratio of y to z is from about 1.5 to about 2.

31. The method of claim 29 wherein x is equal to 0, the oxyalkylene units are formed as random copolymers and the ratio of y to z is from about 1.5 to about 2.

32. The method of claim 27 wherein the hydrocarbyl polyoxyalkylene aminoalcohol is present in an amount from about 10 PTB to about 2000 PTB.

33. The method of claim 31 wherein the hydrocarbyl polyoxyalkylene aminoalcohol is present in an amount from about 40 PTB to about 300 PTB.

34. A hydrocarbyl polyoxyalkylene aminoalcohol compound obtained by the process which comprises reacting a hydroxyl group-containing compound of the general formula $R^1OH$ wherein $R^1$ is an alkyl, alicyclic or alkylalicyclic radical of from about 4 to about 30 carbon atoms or an alkaryl radical wherein the alkyl group contains from about 4 to about 30 carbon atoms with propylene oxide and butylene oxide formed as random copolymers in a mole ratio of from about 1.5 to about 2, there being up to about 50 moles of combined propylene oxide and butylene oxide reacted to provide a hydrocarbyl polyoxyalkylene hydroxide, reacting the hydrocarbyl polyoxyalkylene hydroxide with ammonia to provide a hydrocarbyl polyoxyalkylene amine, and reacting the hydrocarbyl polyoxyalkylene amine with a 1,2-epoxide selected from the group consisting of ethylene oxide, propylene oxide, butylene oxide, pentylene oxide, hexylene oxide and heptylene oxide to provide the hydrocarbyl polyoxyalkylene aminoalcohol.

35. The compound of claim 34 wherein $R^1$ in the hydroxyl group-containing compound $R^1OH$ is the radical

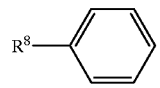

wherein $R^8$ is a hydrocarbyl group of from 4 to about 30 carbon atoms.

36. A fuel composition which comprises a major amount of an internal combustion engine fuel and a fuel combustion deposit-inhibiting amount of at least one hydrocarbyl polyoxyalkylene aminoalcohol of claim 34.

37. A fuel composition which comprises a major amount of an internal combustion engine fuel and a fuel combustion deposit-inhibiting amount of at least one hydrocarbyl polyoxyalkylene aminoalcohol of claim 35.

38. A gasoline additive composition for a gasoline fuel for an internal combustion engine fuel, the additive composition comprising a fuel combustion deposit-inhibiting amount of at least one hydrocarbyl polyoxyalkylene aminoalcohol of the general formula

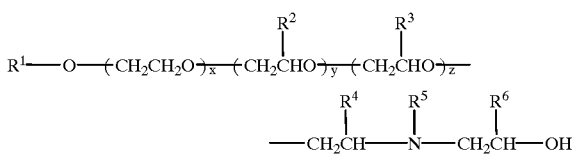

wherein $R^1$ is an alkyl, an alicyclic or an alkylalicyclic radical having from about 4 to about 30 carbon atoms or an alkylaryl where the alkyl group is from about 4 to about 30 carbon atoms; x is an integer from 0 to about 5, y is an integer from 1 to about 49, z is an integer from 1 to about 49 and the sum of x+y+z is equal to 3 to about 50; $R^2$ and $R^3$ each is different and is an alkyl group of from 1 to 4 carbon atoms and each oxyalkylene radical can be any combination of repeating oxyalkylene units to form random or block copolymers; and $R^4$ is the same as $R^2$ or $R^3$; $R^5$ is hydrogen or

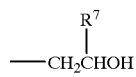

where $R^7$ is hydrogen or an alkyl group of from 1 to 5 carbon atoms and $R^6$ is hydrogen or an alkyl group of from 1 to 5 carbon atoms and at least one additive component selected from the group consisting of antiknock agent, anti-icing additive, antioxidant, metal deactivator and demulsifier.

39. A gasoline additive composition for a gasoline fuel for an internal combustion engine fuel, the additive composition comprising a fuel combustion deposit-inhibiting amount of at least one random hydrocarbyl polyoxyalkylene aminoalcohol copolymer of the general formula

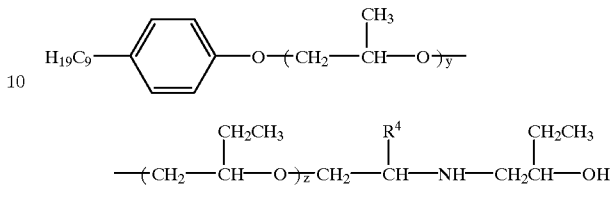

wherein y is an integer from about 5 to about 10, z is an integer from about 5 to about 10 and $R^4$ is —$CH_3$ or —$CH_2CH_3$ and at least one additive component selected from the group consisting of antiknock agent, anti-icing additive, antioxidan, metal deactivator and demulsifier.

40. The gasoline additive composition of claim 39 wherein the ratio of y to z is from about 1 to about 3.

41. The gasoline additive composition of claim 39 wherein the ratio of y to z is from about 1.5 to about 2.

* * * * *

UNITED STATES PATENT AND TRADEMARK OFFICE
CERTIFICATE OF CORRECTION

PATENT NO. : 6,372,000 B1
DATED : April 16, 2002
INVENTOR(S) : DeRosa et al.

It is certified that error appears in the above-identified patent and that said Letters Patent is hereby corrected as shown below:

Column 2,
Line 66, change "$R^3_1$" to -- $R^3$, --.

Column 14,
Line 26, change "4,604,5103" to -- 4,604,103 --.
Line 54 change "i.e," to -- i.e., --.

Column 17,
Line 63, change "i.e," to -- i.e., --.

Column 24,
Line 21, change "antioxidan" to -- antioxidant --.

Signed and Sealed this

Twenty-seventh Day of August, 2002

Attest:

Attesting Officer

JAMES E. ROGAN
Director of the United States Patent and Trademark Office